United States Patent
Rohl et al.

(10) Patent No.: US 11,931,528 B2
(45) Date of Patent: Mar. 19, 2024

(54) ZERO FORCE CATHETER

(71) Applicant: Boston Scientific Scimed, Inc., Maple Grove, MN (US)

(72) Inventors: James P. Rohl, Prescott, WI (US); Aaron Abbott, Columbia Heights, MN (US); Daniel Shuey, Pine City, MN (US); Joel T. Eggert, Plymouth, MN (US); James K. Cawthra, Jr., Ramsey, MN (US); Jay E. Daley, Coon Rapids, MN (US); Christopher Nguyen, Maple Grove, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 471 days.

(21) Appl. No.: 16/891,395

(22) Filed: Jun. 3, 2020

(65) Prior Publication Data
US 2020/0384243 A1    Dec. 10, 2020

Related U.S. Application Data

(60) Provisional application No. 62/858,536, filed on Jun. 7, 2019.

(51) Int. Cl.
*A61M 25/01* (2006.01)
*A61M 25/00* (2006.01)

(52) U.S. Cl.
CPC .... *A61M 25/0147* (2013.01); *A61M 25/0136* (2013.01); *A61M 2025/0002* (2013.01); (Continued)

(58) Field of Classification Search
CPC ...... A61M 25/0136; A61M 2025/0166; A61B 34/30; A61B 34/71; A61B 2034/301; (Continued)

(56) References Cited

U.S. PATENT DOCUMENTS 9,801,679 B2 * 10/2017 Trees ................ A61B 18/1445
11,419,691 B2 * 8/2022 Kim ................ A61B 17/320016
(Continued)

FOREIGN PATENT DOCUMENTS

CA    2582990 A1 * 9/2007 ..... A61B 17/320092
WO    2013180041 A1   12/2013
WO    2017060792 A1   4/2017

OTHER PUBLICATIONS

International Search Report and Written Opinion for the International Patent Application No. PCT/US2020/035865, dated Sep. 23, 2020, 10 pages.

*Primary Examiner* — Laura A Bouchelle
(74) *Attorney, Agent, or Firm* — Seager, Tufte & Wickhem, LLP

(57) ABSTRACT

A catheter configured to dynamically compensate for the impact of internal and external forces that act upon the catheter during use is disclosed. The catheter may include sensors configured to measure received forces on control cables that extend within the catheter. A controller, coupled to the sensors, may record received force measurements associated with a working position of a distal end of the catheter. The controller may monitor subsequently received forces to identify force variances that may deflect the distal end of the catheter from its working position and may apply a driving force to one or more of the control cables to minimize the force variances. Monitoring received forces during use and applying compensating drive forces may reduce deflection of the distal end of the catheter, increasing the accuracy and precision of an annuloplasty procedure while minimizing potential damage to cardiac tissue.

11 Claims, 12 Drawing Sheets

(52) U.S. Cl.
CPC ............... *A61M 2025/0166* (2013.01); *A61M 2210/125* (2013.01)

(58) Field of Classification Search
CPC .. A61B 2090/064; A61F 2/2427; A61F 2/243; A61F 2/2433; A61F 2/2436; A61F 2/2439; A61F 2/2442; A61F 2/2445; A61F 2/2451; A61F 2/2466
See application file for complete search history.

(56) References Cited

U.S. PATENT DOCUMENTS

| | | | |
|---|---|---|---|
| 2002/0087169 A1* | 7/2002 | Brock | A61B 17/0469 606/139 |
| 2005/0060030 A1 | 3/2005 | Lashinski et al. | |
| 2011/0106141 A1* | 5/2011 | Nakamura | A61B 34/71 606/205 |
| 2017/0080581 A1 | 3/2017 | Iida et al. | |
| 2017/0224955 A1 | 8/2017 | Douglas et al. | |
| 2019/0117937 A1 | 4/2019 | Humphrey et al. | |
| 2020/0375682 A1* | 12/2020 | Kincaid | A61B 34/76 |

* cited by examiner

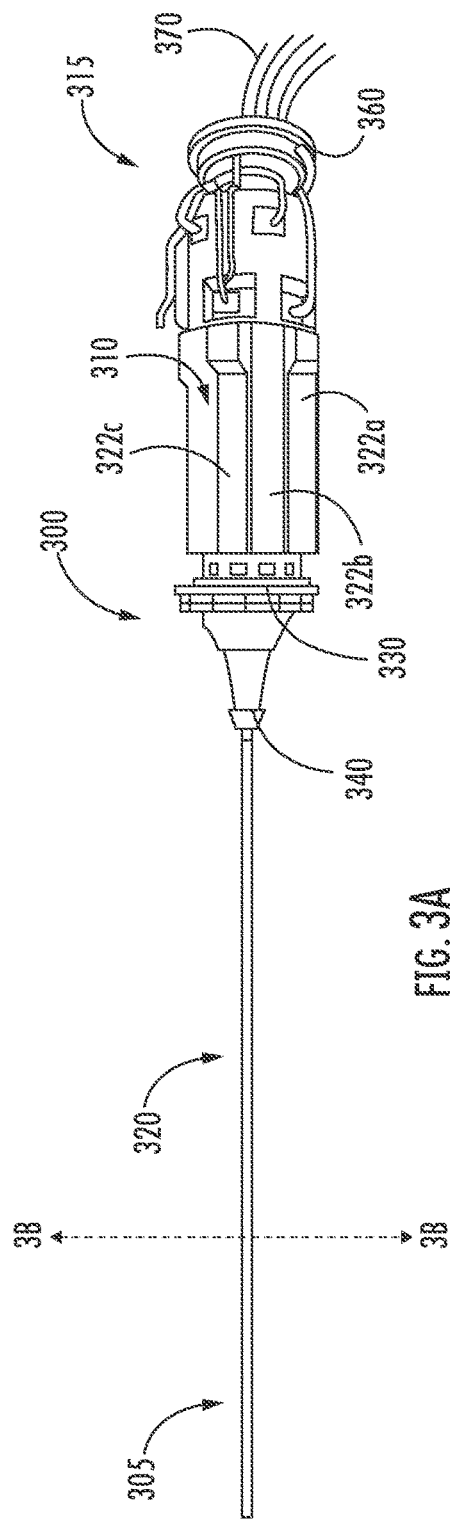
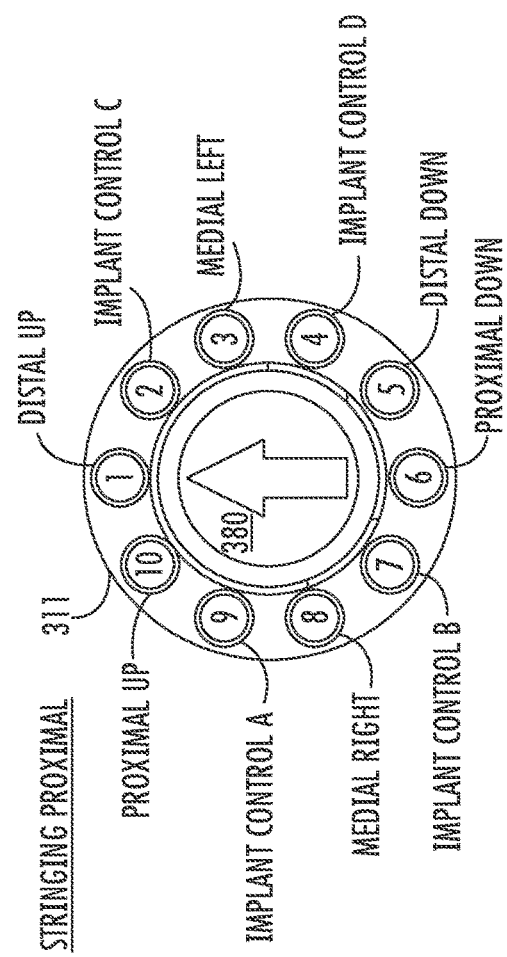
FIG. 3A
FIG. 3B

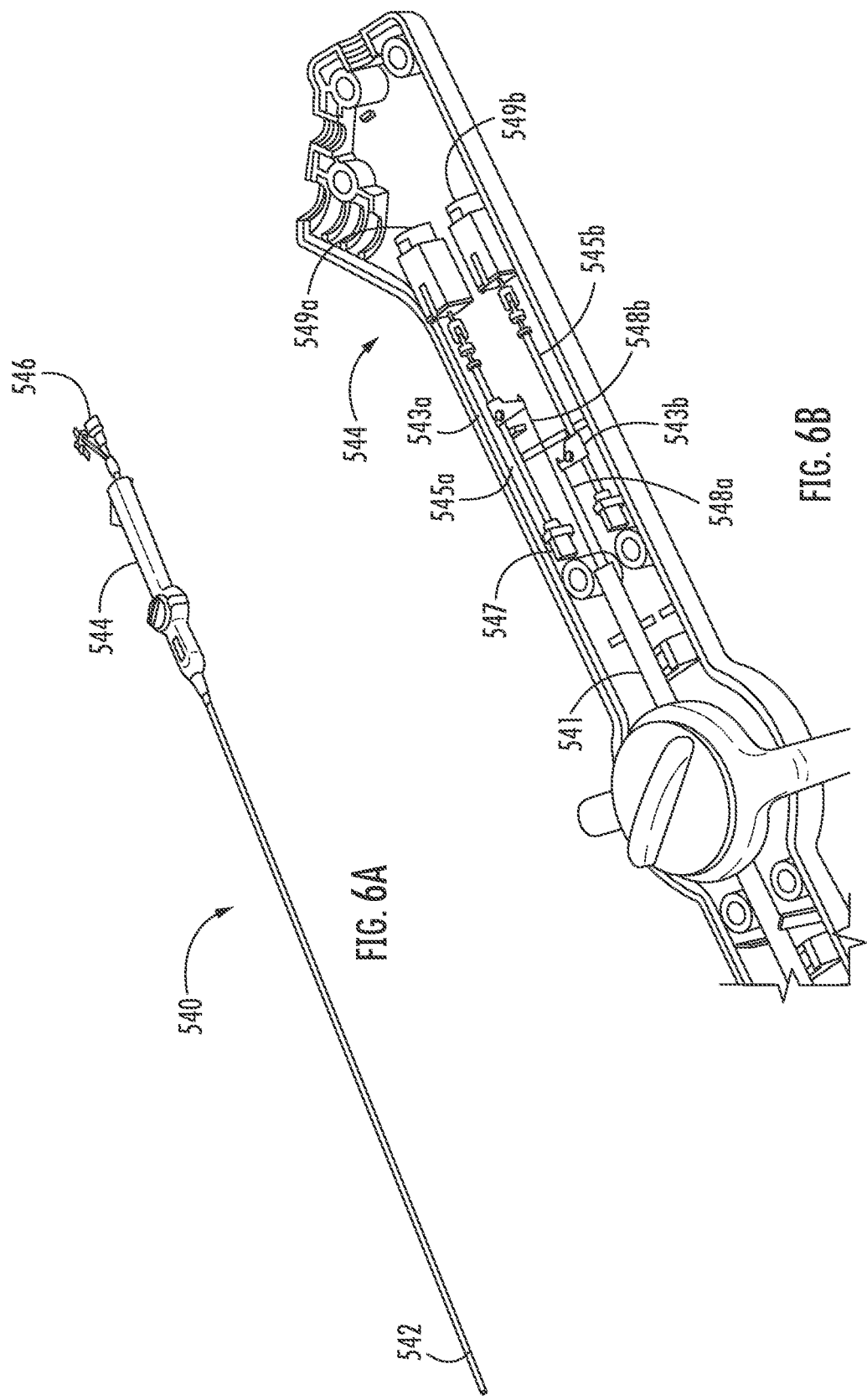

ZERO FORCE CATHETER

CROSS-REFERENCE TO RELATED APPLICATION

The present application claims the benefit of priority under 35 U.S.C. § 119 to U.S. Provisional Patent Application 62/858,536, filed Jun. 7, 2019, which application is incorporated herein by reference in its entirety for all purposes.

FIELD

The present disclosure relates generally to the field of medical devices and more particularly to transluminal surgical procedures.

BACKGROUND

The tricuspid valve lies between the right atrium and the right ventricle of the heart and functions to prevent back flow of blood from the right ventricle into the right atrium. The tricuspid valve is comprised of three leaflets, an anterior leaflet, a posterior leaflet, and septal leaflets. Each leaflet is connected via chordae tendineae to anterior, posterior, and septal papillary muscles of the right ventricle, respectively.

In a healthy heart, the tricuspid valve functions as a one-way valve that closes at ventricular systole to prevent tricuspid regurgitation (TR) of blood into the right atrium. In a diseased heart, tricuspid dilation may cause the valve leaflets to no longer effectively close, or coapt, during systolic contraction. Consequently, regurgitation of blood occurs during ventricular contraction and cardiac output decreases.

The goal of tricuspid repair is to regain valve competence by restoring the physiological form and function of the valve apparatus. One exemplary technique may reduce the valve between the midpoint of the anterior leaflet and the coaptation point to the septum (CS) through clips or other means. Valve repair/replacement may be performed as an open-heart surgery or via endoluminal methods. In either case, arterial Fibrillation (AF) is a common side effect caused at least in part by inadvertent contact with a heart feature, and the associated damage to the cardiac nervous system. Inadvertent contact may result as valve repair components are delivered and positioned about the diseased valve by an annuloplasty catheter. Positioning annuloplasty catheters may be particularly challenging for patients with pacemaker and defibrillator leads. Tricuspid valve tethering, the use of antiplatelet and anticoagulant medications and the high TR recurrence rate may result from or be exacerbated by nervous system damage. It would be desirable to identify a valve repair system that reduces or overcomes these problems by minimizing contact with heart features during annuloplasty procedures.

SUMMARY

Embodiments of the present disclosure relate to a catheter configured to dynamically compensate for the impact of internal and external forces that act upon the catheter during use. With such an arrangement, the catheter may be controlled to minimize deflection of a catheter distal end away from a treatment position, thereby increasing the precision and accuracy of annuloplasty treatment while reducing the potential for inadvertent impact and associated tissue and/or nerve damage.

According to one aspect, a catheter comprises a handle comprising a sensor and a drive mechanism, a shaft coupled to the handle and having a lumen extending therethrough, a cable extending from a distal end of the shaft to the drive mechanism of the handle, the cable operative in response to a drive force applied to the cable by the drive mechanism to perform a distal task and the sensor disposed to measure a force received at the distal end of the cable and to transmit the measured force for use in adjusting the drive force.

In various embodiments, the cable is one of a plurality of cables extending longitudinally within the lumen of the shaft from the distal end of the shaft to the handle, the sensor is one of a plurality of sensors, at least two sensors disposed on one or more cables to measure forces at the one or more cables and the drive mechanism is one of a plurality of drive mechanisms, at least one cable associated with each drive mechanism. The plurality of cables may be disposed about a central lumen that extends longitudinally through a center of the shaft, and wherein the plurality of sensors is disposed about the plurality of cables. The plurality of sensors may be disposed between the plurality of drive mechanisms and the distal end of the shaft. In some embodiments, one sensor is disposed to measure received forces on a single cable. In some embodiments, one sensor is disposed to measure received forces on a plurality of cables.

In various embodiments, the distal task may be associated with a distal position, the distal position is associated with a plurality of measured forces from an associated plurality of sensors when the shaft is in the distal position, and the plurality of measured forces comprise expected distal task forces. In some embodiments, at least one of the drive mechanisms is an annuloplasty drive mechanism configured to drive an annuloplasty cable of the plurality of cables.

In various embodiments, at least two of the drive mechanisms are steering drive mechanisms coupled to drive steering cables of the plurality of cables. The plurality of cables may be circumferentially and/or symmetrically disposed about a central lumen of the shaft.

According to a further aspect, a system comprises a catheter comprising a longitudinal shaft having a proximal end and a distal end and a plurality of cables extending though the longitudinal shaft to the distal end, the plurality of cables coupled at the proximal end of the longitudinal shaft to a handle. The handle may comprise a plurality of sensors disposed about the plurality of cables to sense a respective plurality of received forces at the plurality of cables. The system may include a processor and a non-volatile storage device comprising program code operable when executed upon by the processor to perform various tasks including: record the respective plurality of received forces associated with a distal task position of a distal task as a plurality of expected distal task forces for the distal task and monitor the respective plurality of received forces during the distal task to identify one or more variances between the respective plurality of received forces and the plurality of expected distal task forces. The system includes a controller configured to apply one or more drive forces to the plurality of cables to minimize the one or more variances. In various embodiments, the controller comprises one or more of a joystick, a tablet, a trackball, a keyboard, or a touchpad. In some embodiments the system includes a display for guiding manipulation of the controller to adjust the one or more drive forces applied to the plurality of cables to minimize the variances. In some embodiments, the system includes a visualizer for guiding placement of the distal end of the longitudinal shaft and a selection mechanism enabling association between a visualized position of the distal end of the longitudinal shaft and the expected distal task forces. In some embodiments, the program code further comprises program code operable when executed upon by the processor to automatically adjust the drive forces applied to the plurality of cables to minimize the variances. In some embodiments, the plurality of cables may be circumferentially and/or symmetrically disposed about a central lumen of the longitudinal shaft.

According to a further aspect, a method includes the steps of advancing a distal end of a catheter into a cardiac cavity in a distal task position associated with a distal task, the catheter comprising a drive cable and a sensor disposed upon the drive cable, measuring a received drive cable force when the distal end of the catheter is in the distal task position to identify an expected distal task force, monitoring the received drive cable force during the distal task to determine a variance between the received drive cable force and the expected distal task force and adjusting a drive force applied to the drive cable to minimize the variance. In some embodiments, the catheter further comprises an annuloplasty cable configured to control an annuloplasty task, and the method includes the steps of monitoring a received annuloplasty force during the distal task, determining the variance using the received annuloplasty force and the received drive cable force and adjusting an annuloplasty drive force applied to the annuloplasty cable to minimize the variance. In some embodiments, the step of adjusting includes the step of automatically determining an adjustment to the drive force of the drive cable to compensate for the variance and applying the adjustment to the drive cable. In some embodiments, the drive cable and the annuloplasty cable may comprise two of a plurality of cables disposed longitudinally within a lumen of the catheter, wherein individual positioning forces are be applied to each cable of the plurality to cables to position the distal end of the catheter in the distal task position, and the individual positioning forces are selected to minimize forces applied to the plurality of cables.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3A and 3B illustrate one embodiment of a catheter according to the present disclosure in two perspectives;

FIGS. 6A and 6B illustrate exemplary components of a portion of one embodiment of a catheter configured according to principles disclosed herein;

DETAILED DESCRIPTION

Described herein in one aspect a minimally invasive annuloplasty catheter includes one or more mechanisms to dynamically compensate for the impact of internal and external forces upon the catheter during use. The catheter may include sensors configured to measure received forces on control cables that extend within the catheter. A controller, coupled to the sensors, may record received force measurements associated with a working position of a distal end of the catheter. The controller may monitor subsequently received forces to identify force variances that may deflect the distal end of the catheter from its working position and may apply a driving force to one or more of the control cables to minimize the force variances and retain the distal end of the catheter in the working position. Monitoring received forces and dynamically applying compensating drive forces to counteract force variances minimizes deflection of the distal end of the catheter during use, thereby increasing the accuracy and precision of an annuloplasty procedure while minimizing potential damage to cardiac tissue.

These and other beneficial aspects of the disclosed catheter are now described below. It should be noted that although embodiments of the present disclosure may be described with specific reference to tricuspid valves, the principles disclosed herein may be readily adapted to facilitate reconstruction of any valve annulus, for example including a mitral valve annulus and/or may similarly benefit any other dilatation, valve incompetency, valve leakage, and other similar heart failure conditions.

As used herein, the term "distal" refers to the end farthest away from the medical professional when introducing a medical device into a patient, while the term "proximal" refers to the end closest to the medical professional when introducing a medical device into a patient.

Figure 1:
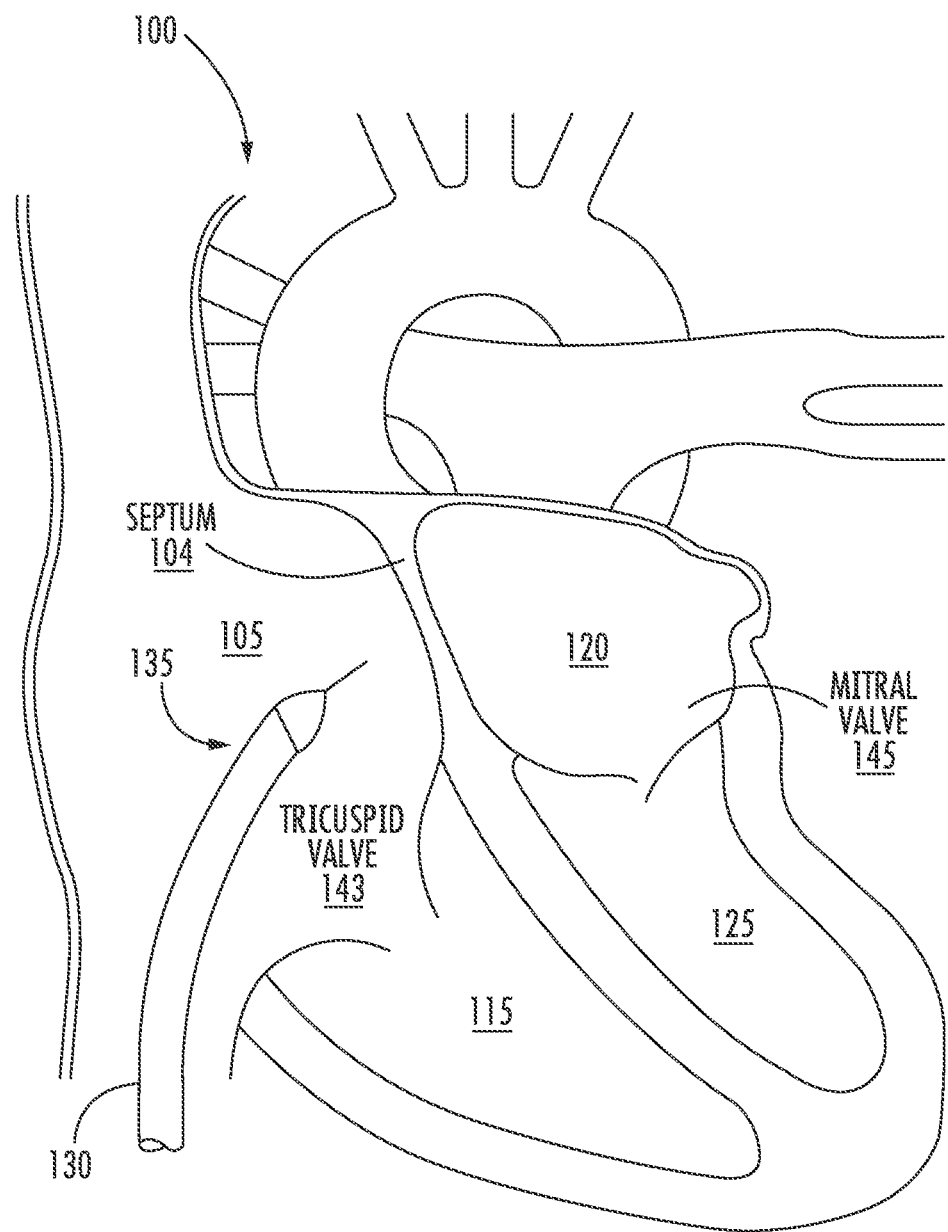
FIG. 1 is a cross section of a heart illustrating an exemplary path of a catheter during an annuloplasty procedure.

FIG. 1 illustrates a cross-sectional depiction of a normal human heart 100. The right side of the heart includes right atrium 105 and right ventricle 115 coupled by tricuspid valve assembly 143. The left side of the heart includes left atrium 120 and left ventricle 125 coupled through mitral valve assembly 145. During an annuloplasty procedure, a catheter may be forwarded transluminally through the femoral artery or the jugular artery to the right atrium 105 for treatment of the tricuspid valve assembly 143 and/or the distal end 135 of the catheter 130 may be advanced through the septum 104 into the left atrium 120 for repair or replacement of the mitral valve assembly 145. In one embodiment, the distal end 135 of the catheter 130 may be steered to a working position proximate to a treatment site associated with a diseased heart feature, and an implant component such as a clip, frame, anchor, or the like, may be deployed from the distal end 135 to the treatment site. In some embodiments, the distal end of the catheter may be capable of being rotationally steered in a range of 360 degrees or more.

A problem arises because the internal and external forces acting on the catheter during implant deployment may cause the distal end of the catheter to deflect away from the working position. Failure to retain the catheter in the working position during implant deployment reduces the precision, accuracy, and effectiveness of the annuloplasty procedure.

Figure 2B:
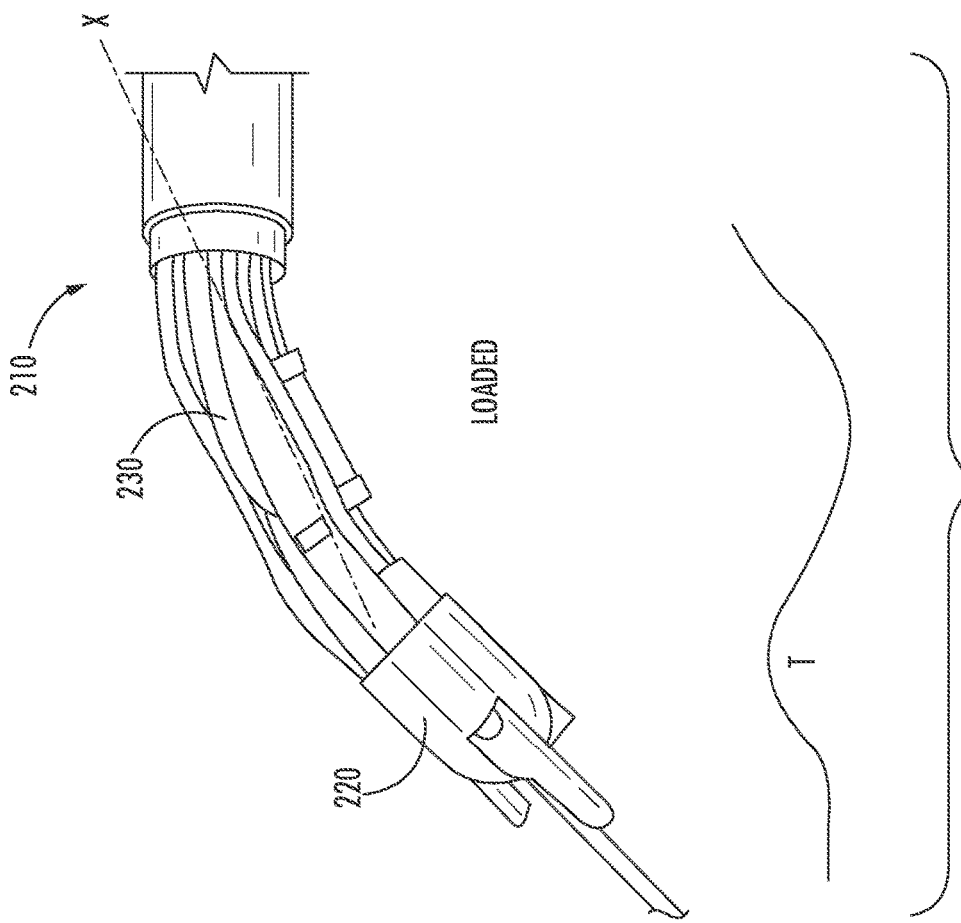
FIGS. 2A and 2B illustrate a distal end of catheter as disclosed herein.
Figure 2A:
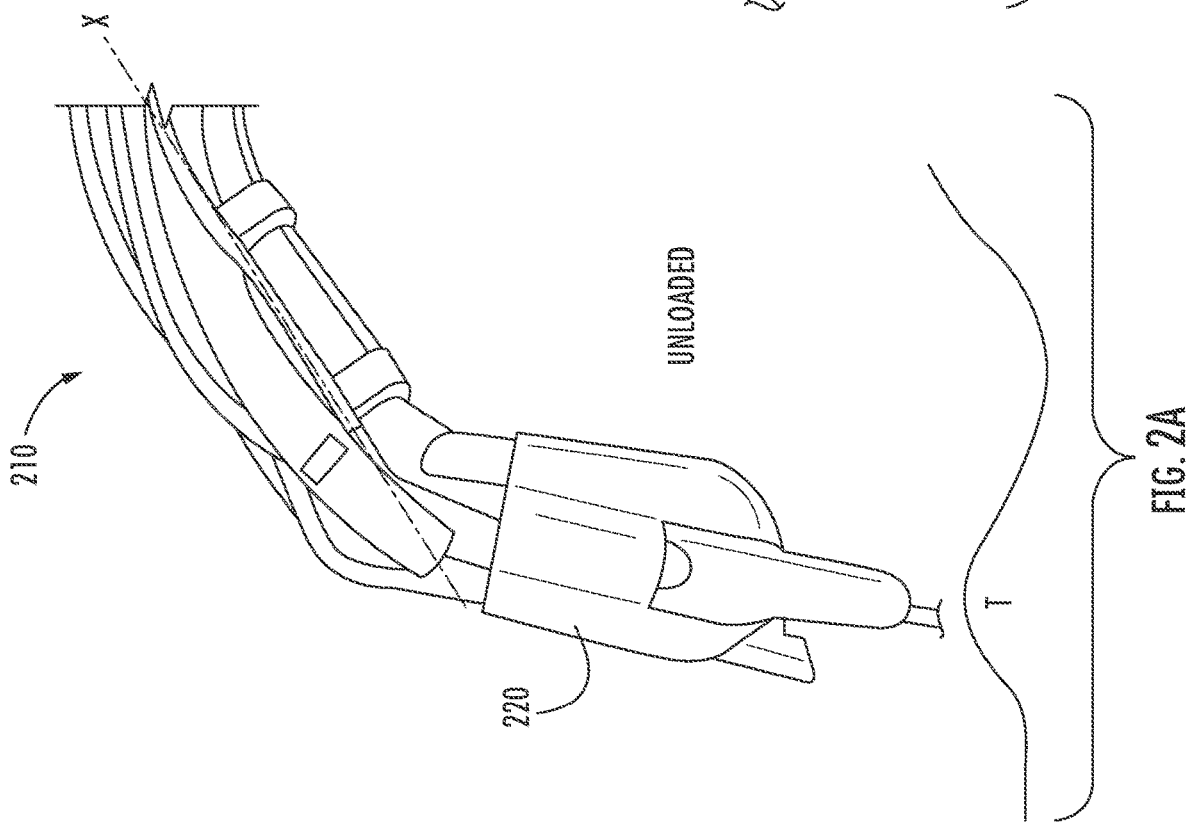

For example, FIGS. 2A and 2B illustrate a potential problem that arises during current annuloplasty procedures. FIG. 2A illustrates a distal end of a steerable catheter 210 which has been steered to a working position wherein the distal end 220 is positioned approximately forty-five (45) degrees from an introduction axis X prior to implant deployment at treatment site T. FIG. 2B illustrates the catheter 210 having an implant component 230 advanced through a lumen of the catheter 210 for deployment. In FIG. 2B it can be seen that the force of the implant on the control cables of the distal end 220 of the catheter causes the distal end to deflect away from the treatment site T, potentially resulting in mis-placed implant components. Forces distally may range from less than about 0.1 lbf to about 2 lbf between an unloaded and loaded distal catheter end, and the high tissue forces of a loaded catheter may result in tissue damage if not adequately controlled/maintained. However, difficulties arise because controlling distal forces in the range of less than about 0.1 lbf to about 2 lbf may require proximal control of tensions as high as 10-20 lbf. Management of high tensions increases the difficulty of making small movements within the heart cavity.

A catheter as disclosed herein overcomes these issues through real-time monitoring of internal and external forces on catheter drive cables. Monitored force information may enable manual and/or automatic adjustment of the cable drive forces to facilitate control of a working position of the distal end of the catheter in the presence of internal and external forces. FIG. 3A illustrates one embodiment of an annuloplasty catheter 300 configured to monitor internal and external forces exerted upon the catheter during use for the purposes of adjusting such forces (manually and/or automatically) to maintain catheter position with minimal loading on the catheter. The catheter 300 is shown to comprise a handle 310 disposed at a proximal end 315 and a shaft 320 extending from the handle 310 to a distal shaft end 305. The handle 310 is comprised of a plurality of sensors 322a, 322b and 322c, coupled via a connector ring 330 to a yoke 340 at the handle distal end, and to tether ring 360 at a handle proximal end. Tether ring 360 corrals a plurality of control cables 370, which extend through the proximal end of the handle towards the distal end 305 of the shaft 320. The control cables 370 may be coupled to a controller (not shown) configured to apply a drive force or other load, torque, compression or tension to the plurality of cables (either individually or in combination) to control a distal task at the distal end 305 of the shaft.

According to one aspect, each sensor 322a includes a housing comprising an external surface and an internal surface, with the internal surface of the housing disposed circumferentially about a central longitudinal axis of the handle 310. The sensor may comprise a measuring device mounted on an internal face of the housing and configured to measure a force (e.g., tension, compression) on one or more of the control cables. According to one aspect, the measured force may be communicated to and/or sampled by a controller (not shown) coupled to the catheter 300 and used to control a drive force administered to the drive cables 370.

FIG. 3B illustrates a cross section the catheter shaft taken along axis 3B-3B of FIG. 3A. In one embodiment, a plurality of control cables 1-10 are disposed within a sheath 311 of the shaft 320, surrounding a central lumen 380 through which implant components may be deployed during use. The control cables 1-10 may operate individually or in coordination to perform a distal task, such as a steering distal task or an annuloplasty distal task. For the purpose of this disclosure, a distal task shall include a variety of tasks performed alone or in combination, including but not limited to a deflection task, a positioning task, a rotation task, a pushing task, an anchoring task, a suturing task, a clipping task, a clamping task, a cinching task, a compression task, an expansion task, and the like. For example, in the embodiment of FIG. 1, control cables 1, 3, 5, 8 and 10 may comprise deflection cables such as Bowden cables, each deflection cable configured to deflect respective cable in a particular direction away from its longitudinal central axis. Deflection cables may, for example, cause the distal ends of the respective cable to lift up, down, medially left, medially right. Deflection cables may be configured to cause the proximal ends of the cable to move up or down.

The control cables may also include one or more implant control cables. The implant control cables may, for example, release or deploy implant components, rotate implant components, compress or expand implant components, or otherwise manipulate and/or control implant components.

In various embodiments, sensors may be disposed between the drive mechanisms of the control cable and the distal end of the shaft. The sensors may be configured to obtain force measurements at one location of one cable, at multiple locations of a single cable, at one location of multiple cables, and/or at multiple locations of multiple cables. Force measurements may be taken from all of the control cables or a subset of all of the control cables. In some embodiments, counteracting drive forces may be determined based upon only measured forces from steering control cables, only measured forces from annuloplasty control cables, or a combination thereof.

Although ten control cables are shown in FIG. 3B, the present disclosure is not limited to a system including ten control cables and/or ten sensors, and it is recognized that the number of control cables capable of being disposed within a catheter is limited only by the dimensions of the catheters and the dimension and number of the control cables.

Figure 4:
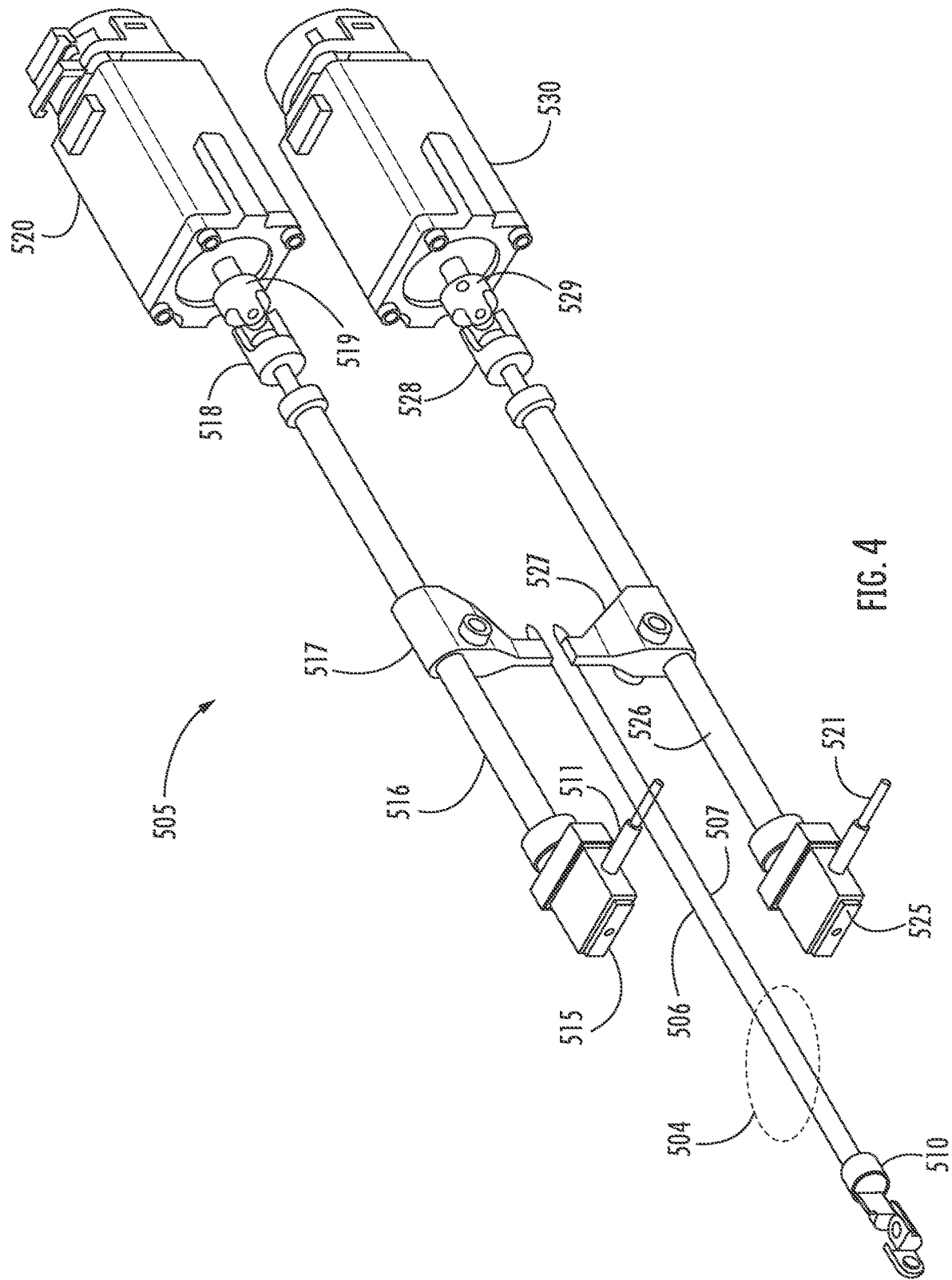
FIG. 4 is a diagram of one embodiment of a portion of the catheter according to the present disclosure.

FIG. 4 illustrates exemplary components that may be included within a catheter to monitor and/or adjust internal and/or external forces exerted upon a drive cable 504. The components include drive cable 504 (comprising two portions 506 and 507) coupled at either end to tensile grips 517 and 527 which are disposed along respective floating screws 516, 526.

Each floating screw 516, 526 comprises a drive coupler 518, 528 disposed at a proximal end, and a load cell sensor 515, 525 disposed at a distal end. Tensile grips 517, 527 are translatably disposed upon the respective floating screws 516, 526. In one embodiment, the drive couplers 518, 528 are configured to matingly engage with the drive couplers 519, 529 of motors 520, 530 to rotate the respective floating screws 516, 526 to thereby translate the tensile grips 517, 527 axially along the floating screws. Translation of the tensile grip 517 along floating screw 516 modifies the tension of distal UP cable 506, while translation of tensile grip 527 along the floating screw 526 modifies the tension of distal DOWN cable 507 to thereby affect the position of the distal end 510 of the catheter 505.

According to one aspect, load cell sensors 515, 525 are disposed at respective distal end of the floating screws 516, 526. In one embodiment, the load cell sensors may comprise an arm 511, 521 which extends from the load cell sensor and rest upon the drive cable 504 to measure the forces upon the drive cable. Although arms are shown, it is understood that various other methods of providing measurement contact between the drive cable 504 and the sensors may be substituted herein. During operation, internal and external forces that impinge upon the cables 504 can be measured by the load cell sensors 515, 525. A load cell sensor that may be used herein includes, for example, a FUTEK load cell sensor model LSB200, manufactured by FUTEK Advanced Sensor Technology Inc., of Irvine California, or similar device. The measurements may be used to advance and/or retract the respective tensile grips 517, 527 along the respective floating screws 516, 526 to adjust the tensions to maintain a desired position of the distal end 510 of the catheter 505 as described in more detail below.

It should be noted that although a particular drive motor 520, 530 is shown in FIG. 4, the catheter solution disclosed herein is not dependent upon any particular form of drive motor. Various embodiments of zero force catheters disclosed herein disclose manual drive control (e.g., using knobs, levers, or the like) and motorized drive controllers. In addition, disclosed embodiments include motorized controllers that are manually controlled and those that are automatically controlled via software or the like.

According to one aspect the catheter disclosed herein is referred to as a 'zero force' catheter configured to monitor received forces during use and apply compensating drive forces to maintain a position of a distal end of the catheter to reduce deflections caused by internal and external forces acting upon the catheter during use.

Figure 5A:
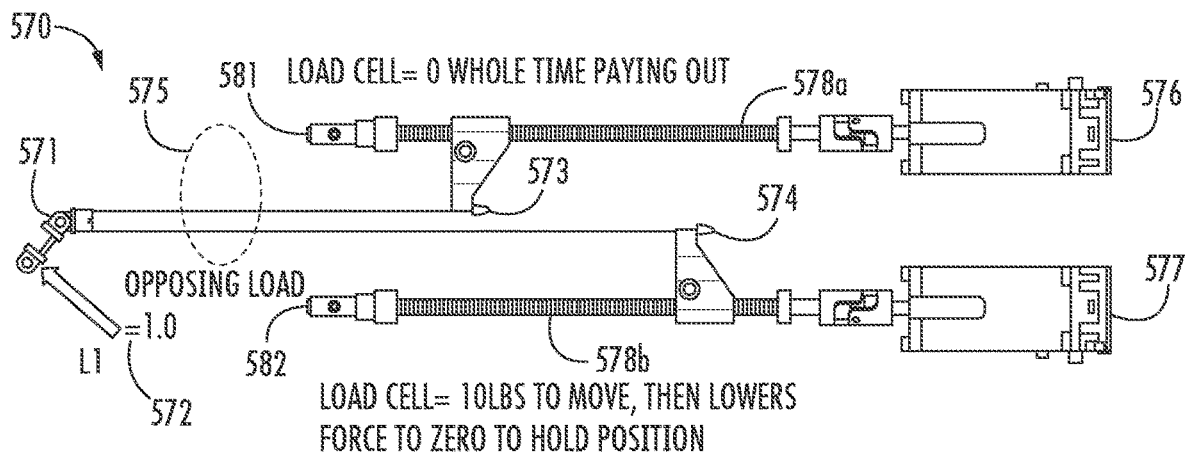
FIGS. 5A and 5B illustrate exemplary components of a portion of one embodiment of a catheter configured according to principles disclosed herein.
Figure 5B:
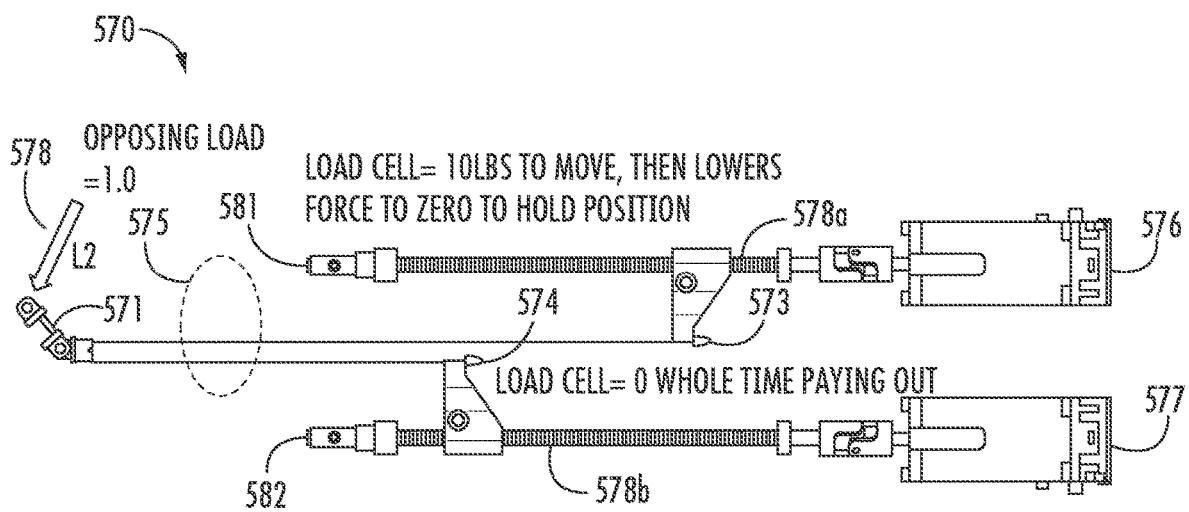

FIGS. 5A and 5B illustrate exemplary embodiments and methods of operation of a zero force catheter as disclosed herein. In FIG. 5A, the distal end 571 of catheter 570 is shown positioned to experience an opposing load L1 of 1.0 lbf upon cables 575 associated with a working position. To reach this position, grip 573 may be translated distally along floating screw 578a, while grip 574 may be translated proximally along floating screw 578b by activation of motors 576, 577. According to one aspect, once the working position is identified, the relative forces upon the cables may be measured by sensors 581, 582 saved as baseline forces associated with a 'zero' position of the catheter.

In FIG. 5B, during use, internal and external forces L2 may impinge upon the distal end 571 of catheter 570. Such forces are measured by sensors 581, 582. Translation of the grips 573, 574 along the floating screws 578a, 578b may be controlled to provide forces that counteract the forces L2 upon the distal end, to return the distal end 571 to the position shown in FIG. 5A. For example, grip 573A may be moved proximally along floating screw 578a, while grip 574b may be moved distally along floating screw 578b.

FIGS. 6A and 6B illustrate one embodiment of a catheter 540 according to aspects disclosed herein, comprising a shaft 543 disposed between a distal end 542 and a handle 544. Positioning and steering of the distal tip 542 are controlled via manual mechanisms 546, including dials, thumbwheels, or other manual manipulation mechanisms. According to one aspect, the catheter 540 comprises force measurement mechanisms such as those described with regard to FIG. 4 disposed within handle 544. The mechanisms include floating screws 545a, 545b, sensor 547 and drivers 549a, 549b (which may comprise motorized and/or manual driving mechanisms). The cables 548a, 548b are shown coupled on a first end to the floating screws 545a, 545b via grips 543a, 543b and extending at a second end through a sheath 541 to the distal end of the catheter. In one embodiment, during use, the measured force may be displayed to a user (e.g., for example, on a display of handle (544), enabling a user to manually adjust the respective drivers 549a, 549b to maintain a distal tip position as described below.

Figure 7:
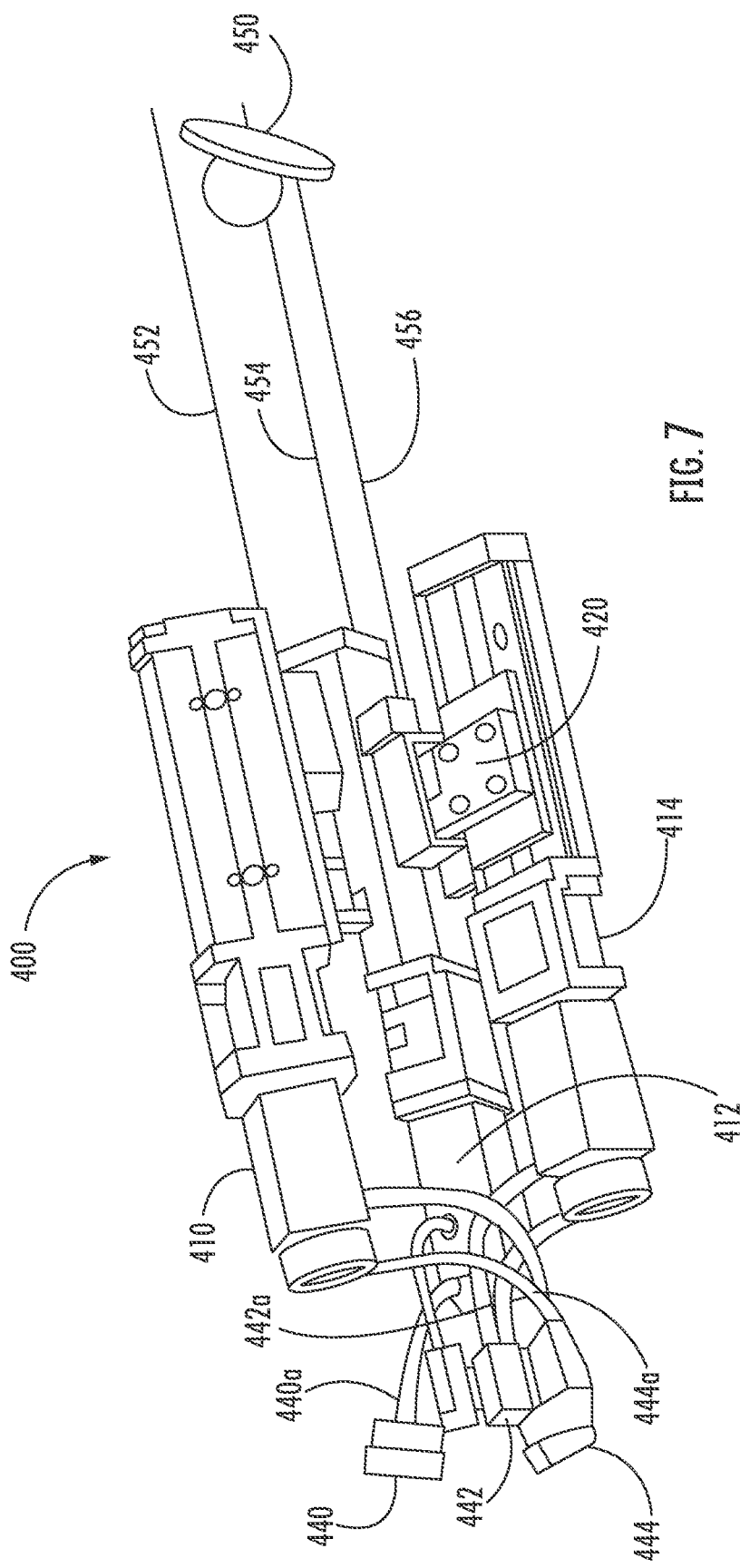
FIG. 7 illustrates exemplary components of a handle of one embodiment of a catheter disclosed herein.

FIG. 7 is a view of a portion of an alternative embodiment of a catheter handle 400 illustrating three sensor housings 410, 412, and 414, each sensor housing having a sensor 420 positioned such that it is in measurement contact with control cable 456. In FIG. 4, gimbal 450 is an illustrative representation of the distal end of the catheter, intended to display how the application of drive forces to control cables 454 and 456 may be used to pivot or otherwise direct the distal end of the catheter. In FIG. 7, control cables 454 and 456 comprise steering cables, and control cable 452 may control another distal task of the catheter. In one embodiment, the measured force information provided by the sensors may be forwarded to a controller via connectors 440b, 442b, and 444b, which may be coupled to the sensors by wires 444a, 442a, and 440a. In other embodiments, the sensors may comprise wireless sensors configured to wirelessly transmit measured force information to a controller.

Figure 8:
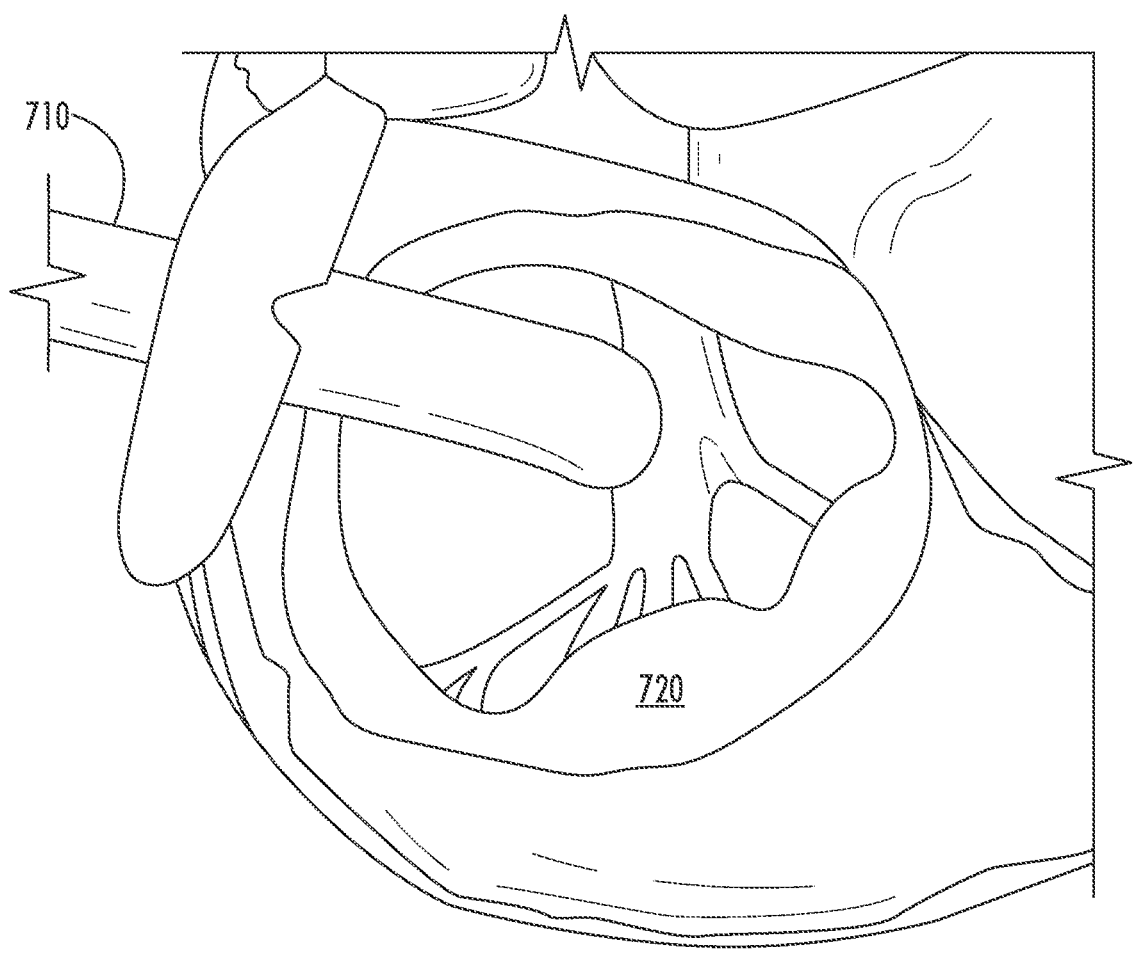
FIG. 8 is a top down view of a heart valve including a positioned catheter.

FIG. 8 is a top down view illustrating a catheter 710 disposed in a working position associated with a distal task over a diseased valve 720. In one embodiment, the distal task may be an annuloplasty repair task which further includes the distal task of steering the distal end of the catheter to a working position for the annuloplasty procedure. For some annuloplasty procedures, the working position may be one as shown in FIG. 8, wherein the distal tip of the catheter 710 has been steered into a position that is relatively aligned with a central axis extending normally from a center of the valve. According to one aspect, once the catheter has been moved into a desired working position, the measured forces experienced by one or more of the control cables when the distal end of the catheter is in the working position may be recorded as baseline, expected force measurements associated with the working position. As disclosed, during the annuloplasty procedure the controller may monitor the force measurements of the cables and apply drive forces to compensate for variances from the expected force measurements. For example, the controller may increase the tension on one cable to decrease the tension on another cable that is undesirably deflecting the distal end of the catheter away from the target treatment site.

Figure 9:
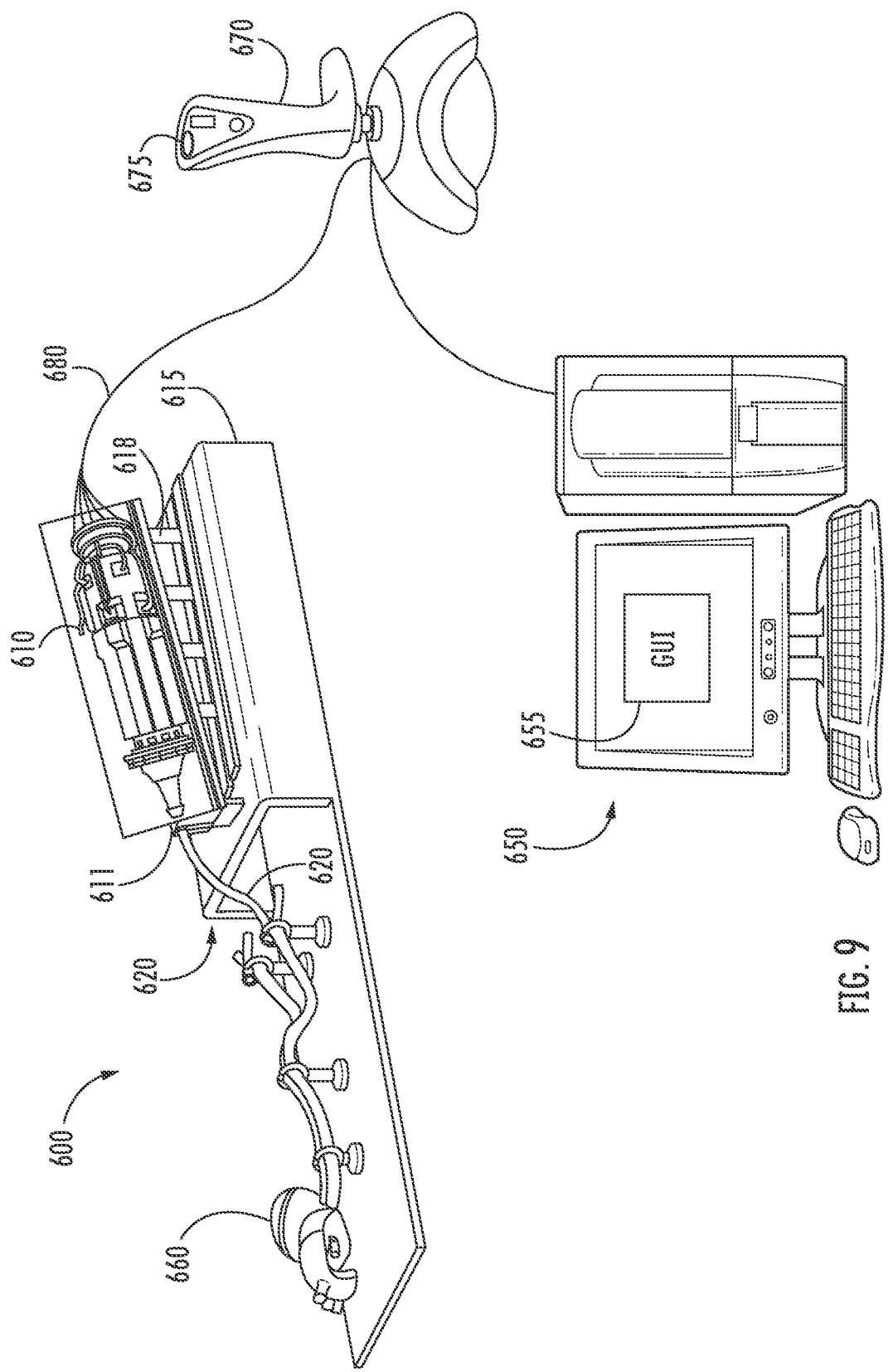
FIG. 9 is one embodiment of a system comprising an embodiment of a catheter disclosed herein.

FIG. 9 illustrates a system 600 including a catheter 620 as disclosed herein. The catheter 620 includes a handle 610 disposed upon a handle support 618 of a stage 615. A mounting clip 611 may couple to the yoke of the handle 610, to securely the handle to the support 618. Catheter 620 may extend from the handle 610 transluminally to heart 660.

Control cable drive wires 680 may extend from the proximal end of the handle 610 to a controller, where the controller comprises of a joystick 670 coupled to a processing device 650. The processing device may be, for example, a personal computer, workstation, laptop, tablet, mobile device, or similar devices. In one embodiment, the processing device 650 may comprise a central processing unit and include or be coupled to a non-volatile storage device configured to execute at least a force monitoring process wherein the forces exerted upon control cables are monitored and displayed at a graphic user interface (GUI) 655. In some embodiments, the monitored forces are displayed as offsets from a baseline plurality of forces associated with the working position; i.e., wherein the working position represents a 'zero force' position of the working catheter, and deviations from the baseline are adjusted to bring the forces back to the zero force position.

Figure 10:
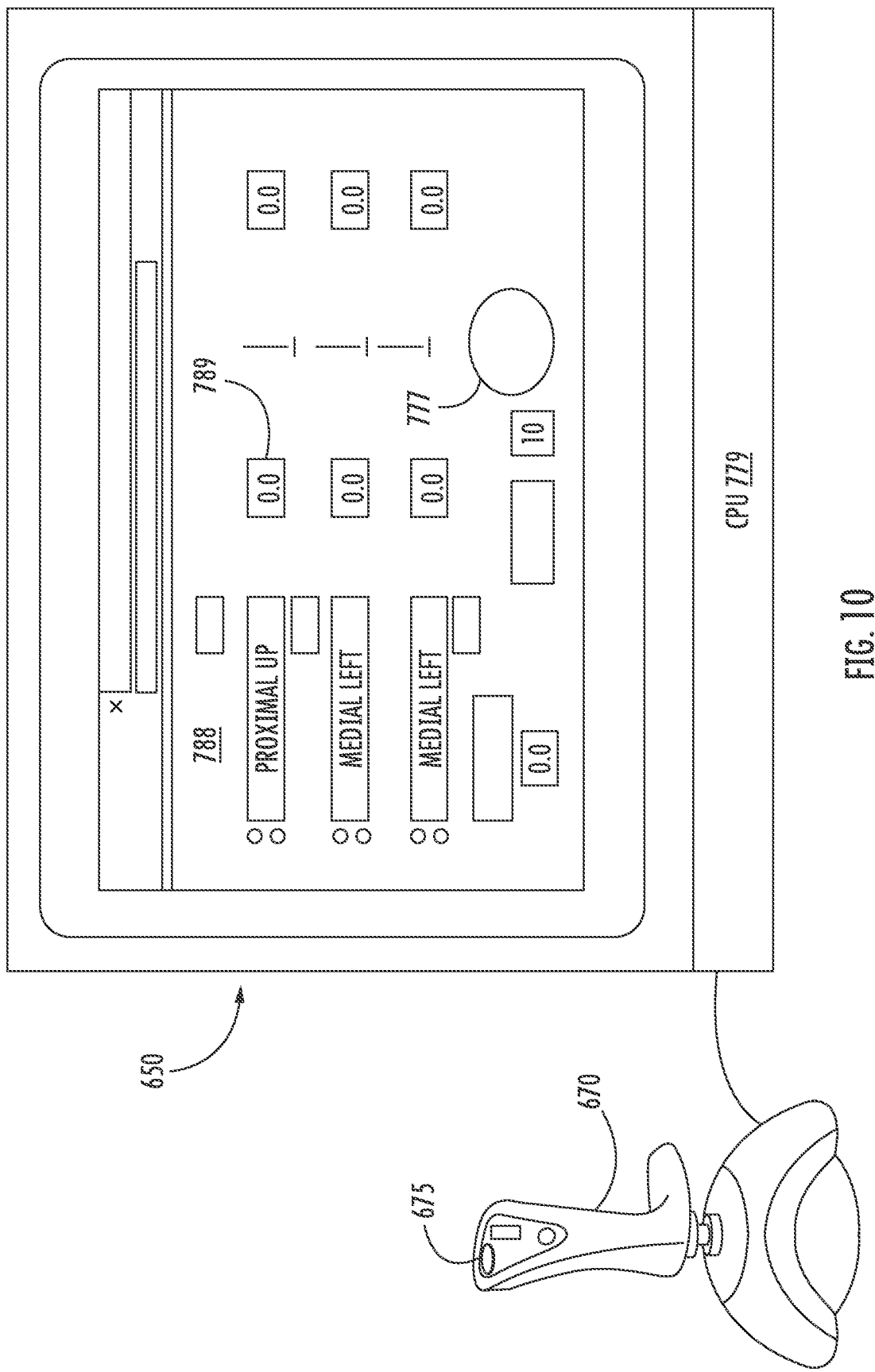
FIG. 10 illustrates an exemplary user interface that may provide guidance as disclosed herein.
Figure 11:
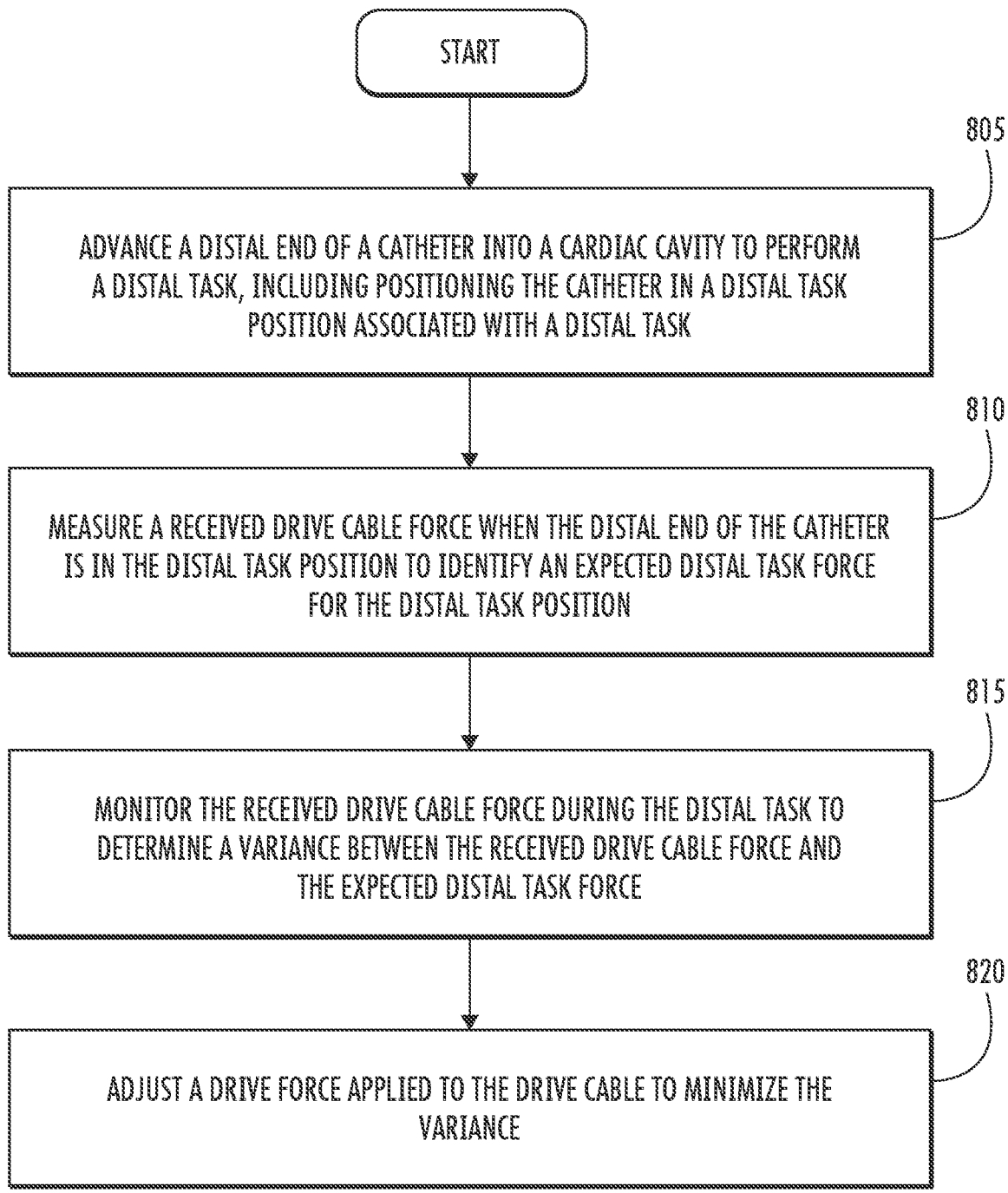
FIG. 11 is a flow diagram provided to illustrate exemplary steps that may be performed in one embodiment disclosed herein.

In one embodiment, the control cable drive wires 680 may be coupled to a joystick or other similar mechanism, including, but not limited to a trackball, a tablet, a keyboard, a touchpad, a tablet, or the like. The control cable drive wires 680 may be directly coupled to the joystick 670 as shown in FIG. 9, or alternatively may communicate using a wireless protocol, such Bluetooth, WIFI, or the like. In some embodiments, the joystick controller may include processing circuitry configured to translate movement of the handle of the joystick into torque or compression forces on the plurality of cables, i.e., to provide drive forces to the plurality of cable 680. In some embodiments, a display presented on the GUI 655 may be relate the position of the joystick and the associated forces exerted on the plurality of control cables by the position of the joystick to the zero force position of the working catheter. For example, FIG. 10 illustrates an exemplary GUI 755 executing on a CPU 779 and is shown to include one or more dials 777 configured to indicate variances in forces from the 'zero force' position of the catheter. A user may use the feedback provided by the GUI 755 to manage a position of the joystick. In one embodiment, the button 675 of the joystick may be used to lock the control cable forces such that inadvertent motion of the joystick does not affect the catheter.

The user interface may provide further feedback to the user to assist the user to better comprehend the position of the distal end of the shaft in a three dimensional space. For example, the GUI may include a scale 788 illustrating which control cables are currently activated and their relative degree of activation. The GUI may also display individual force variance measurements for example in box 789.

It should be noted that, although a particular GUI arrangement is shown various users may prefer different forms of feedback. GUIs including multiple dials 777 for joystick navigation, and or different mechanisms for imparting similar information that may be used to adjust forces to return a distal end of a catheter to a working, zero force position, are considered within the scope of the present disclosure.

In some embodiments, a mechanism may be provided as part of the GUI or other controller mechanism to identify a distal catheter position as a working position to use as the zero force position. The mechanism may include, but not be limited to, a button on joystick 670, a keyboard entry, a touchscreen entry or other similar method.

An alternate embodiment uses program code of the controller to control a process for dynamically determining and applying compensating drive forces to one or more control cables to retain the distal end of the working catheter in the zero force working position. FIG. 8 illustrates exemplary steps that may be performed by such a process. At step 805, the distal end of the catheter may be advanced into a cardiac cavity of a heart to perform a distal task, such as an annuloplasty task, including a positioning task. At step 810, the controller measures and stores the received drive cable forces as expected drive cable forces for the distal task. At step 815 the controller monitors the received drive cable forces and compares the received drive cable forces against the expected drive cable forces to identify one or more variances. At step 820 the controller automatically identifies adjustments for one or more drive forces that would reduce the variances in forces experienced by the control cables.

For example, the controller may examine the measured forces of all measured control cables and adjust a drive force on one or more cables by increasing and/or decreasing the drive force to relieve the tension causing the deflection.

Monitoring received forces and counteracting force variances, whether manually or automatically, minimizes deflection of the distal end of the catheter during use, thereby increasing the accuracy and precision of an annuloplasty procedure while minimizing potential damage to cardiac tissue.

Figure 12:
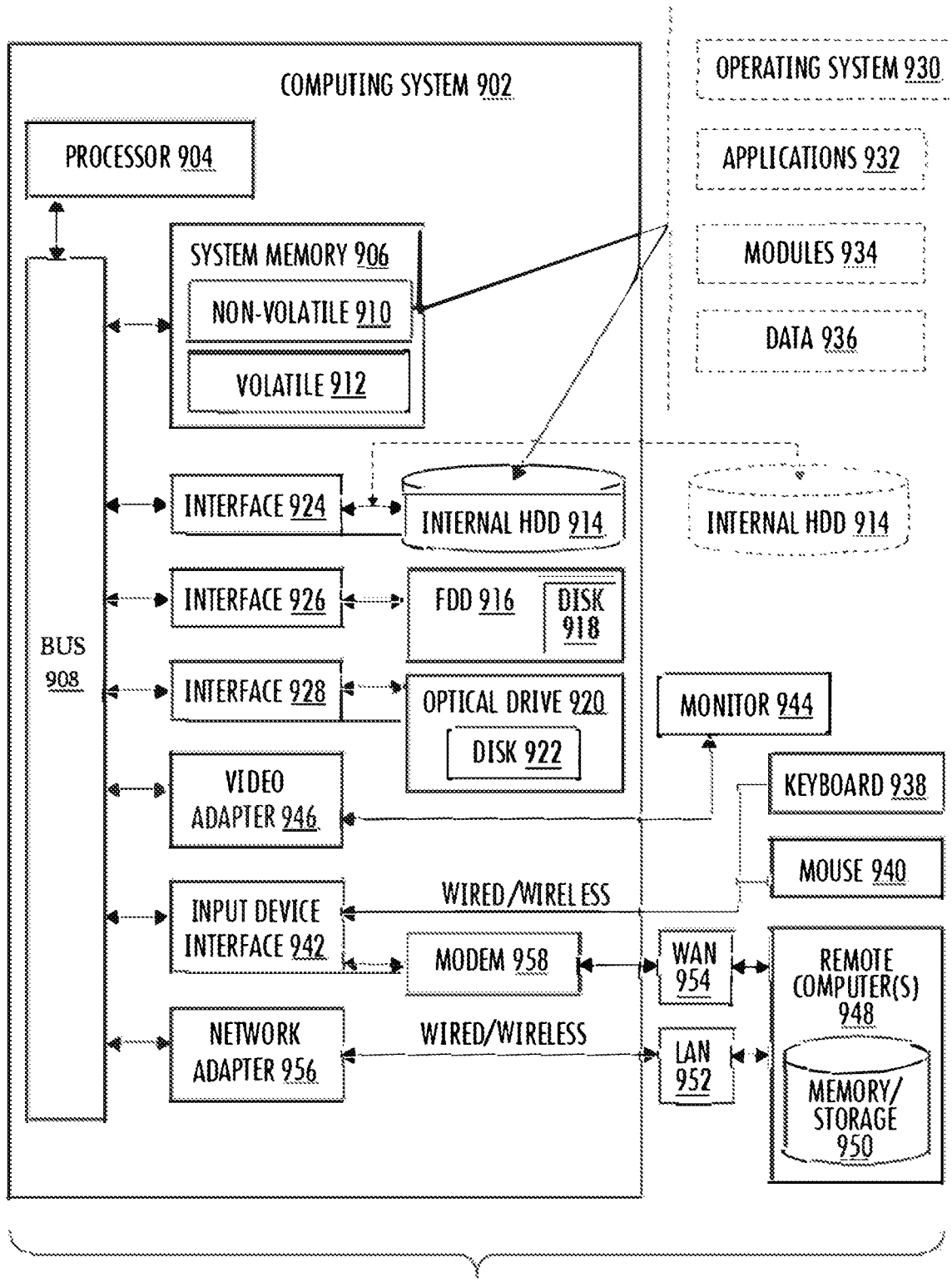
FIG. 12 is an illustration of an exemplary computing processor that may be used to control various aspects of the catheter as disclosed herein.

FIG. 12 illustrates an embodiment of an exemplary computing architecture 900 of a processing system 650 or a joystick 670 of the controller. In various embodiments, the computing architecture 900 may comprise or be implemented as part of an electronic device that includes greater or fewer of the components shown in FIG. 9. The computing architecture 900 is configured to implement all logic, applications, systems, methods, apparatuses, and functionality described herein.

The computing system 902 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing system 902.

As shown in FIG. 12, the computing system 902 comprises a processor 904, a system memory 906 and a system bus 908. The processor 904 can be any of various commercially available computer processors. Dual microprocessors, multi-core processors, and other multi-processor architectures may also be employed as the processor 904.

The system bus 908 provides an interface for system components including, but not limited to, the system memory 906 to the processor 904. The components may be controlled by interfaces, for example disk devices may be controlled according to their various protocols by interfaces 924, 926, and 928. Network communications may be controlled by network adapter 956. The system memory 906 may include various types of computer-readable storage media in the form of one or more higher speed memory units including non-volatile memory 910 and/or volatile memory 912. A basic input/output system (BIOS) can be stored in the non-volatile memory 910.

The computing system 902 may include various types of computer-readable storage media in the form of one or more lower speed memory units, including an internal (or external) hard disk drive (HDD) 914, a magnetic floppy disk drive (FDD) 916 to read from or write to a removable magnetic disk 918, and an optical disk drive 920 to read from or write to a removable optical disk 922 (e.g., a CD-ROM or DVD). The drives and associated computer-readable media provide volatile and/or nonvolatile storage of data, data structures, computer-executable instructions, and so forth. For example, a number of program modules can be stored in the drives and memory units 910, 912, including an operating system 930, one or more application programs 932 including a drive controller program as described with regard to FIG. 8, other program modules 934, and program data 936. For example, the controller program may store program data including the expected plurality of received distal forces associated with a zero-force/working position in a storage device of the processor.

A user can enter commands and information into the computing system 902 through one or more wire/wireless input devices, for example, a keyboard 938 and a pointing device, such as a mouse 940. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processor 904 through an input device interface 942 that is coupled to the system bus 908 but can be connected by other interfaces.

A monitor 944 or other type of display device is also connected to the system bus 908 via an interface, such as a video adaptor 946. The computing system 902 may operate in a networked environment using logical connections via wire and/or wireless communications to one or more remote computers, such as a remote computer 948 including a memory/storage device 950. The logical connections depicted include wire/wireless connectivity to a local area network (LAN) 952 and/or larger networks, for example, a wide area network (WAN) 954. The computing system 902 may also be operable to communicate with wired and wireless devices or entities using the IEEE 802 family of standards. One or more aspects of at least one embodiment may be implemented by representative instructions stored on a machine-readable medium which represents various logic within the processor, which when read by a machine causes the machine to fabricate logic to perform the techniques described herein.

Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination. Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). understood to include the possibilities of "A" or "B" or "A and B."

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A catheter comprising:
   a handle comprising a sensor and a drive mechanism;
   a shaft extending from the handle to a distal shaft end, and having a lumen extending therethrough;
   a task cable extending from the drive mechanism to the distal shaft end to perform a task in addition to or instead of steering at the distal shaft end, in response to a drive force applied to the task cable by the drive mechanism; and
   an additional cable coupled to an implantable device to control the implantable device;
   wherein the sensor measures a force received at the distal end of the task cable and transmits the measured force to the drive mechanism for use in adjusting the drive force applied by the drive mechanism to the cable to perform the task at the distal shaft end.

2. The catheter of claim 1, wherein:
   the task cable comprises two portions extending from the handle to the distal end of the shaft;
   the sensor comprises a sensor for each portion of the task cable to measure forces independently at the two portions of the task cable; and
   the drive mechanism comprises a drive mechanism for each portion of the task cable associated therewith to adjust the drive force applied to each portion of the task cable independently of the other portion of the task cable.

3. The catheter of claim 1, wherein:
   the task cable comprises a plurality of cables disposed about the shaft lumen;
   the sensor comprises a plurality of sensors disposed about the plurality of cables;
   and the drive mechanism comprises a plurality of drive mechanisms with at least one of the plurality of cables associated with each drive mechanism.

4. The catheter of claim 3, wherein the plurality of sensors is disposed between the plurality of drive mechanisms and the distal shaft end.

5. The catheter of claim 3, wherein one sensor is disposed to measure received forces on a single one of the plurality of cables.

6. The catheter of claim 3, wherein one sensor is disposed to measure received forces on the plurality of cables.

7. The catheter of claim 3, wherein the task cable further performs a steering task.

8. The catheter of claim 3, wherein at least one of the drive mechanisms is an annuloplasty drive mechanism configured to drive an annuloplasty cable of the plurality of cables.

9. The catheter of claim 1, wherein at least two of the drive mechanisms apply a drive force to the task cable at the shaft distal end to perform one or more tasks selected from the group consisting of a deflection task, a positioning task, a rotation task, a pushing task, an anchoring task, a suturing task, a clipping task, a clamping task, a cinching task, a compression task, an expansion task.

10. The catheter of claim 3, wherein the plurality of cables is circumferentially and/or symmetrically disposed about the shaft lumen.

11. The catheter of claim 1, wherein a distal end of the task cable extends past the shaft.

\* \* \* \* \*